United States Patent [19]
Jobe

[11] Patent Number: 5,785,713
[45] Date of Patent: Jul. 28, 1998

[54] SURGICAL FIXATION APPARATUS

[76] Inventor: Richard P. Jobe, 26985 Orchard Hill La., Los Altos Hills, Calif. 94022

[21] Appl. No.: 852,012

[22] Filed: May 6, 1997

Related U.S. Application Data

[63] Continuation-in-part of Ser. No. 428,913, Apr. 25, 1995, Pat. No. 5,634,926.

[51] Int. Cl.⁶ .................................................. A61B 17/58
[52] U.S. Cl. ........................ 606/69; 606/68; 606/75; 606/78; 606/151; 606/70; 606/72; 606/73; 606/101
[58] Field of Search .................... 606/60, 69, 75, 606/77, 78, 139, 151, 70, 71, 72, 73, 54, 101

[56] References Cited

U.S. PATENT DOCUMENTS

| | | | |
|---|---|---|---|
| 3,939,828 | 2/1976 | Mohr et al. | 128/92 B |
| 4,655,203 | 4/1987 | Törmälä et al. | 128/92 YP |
| 4,841,960 | 6/1989 | Garner | 606/75 |
| 4,960,420 | 10/1990 | Goble et al. | 606/72 |
| 5,053,038 | 10/1991 | Sheehan | 606/75 |
| 5,057,111 | 10/1991 | Park | 606/69 |
| 5,167,665 | 12/1992 | McKinney | 606/75 |
| 5,290,281 | 3/1994 | Tschakaloff | 606/28 |
| 5,443,482 | 8/1995 | Stone et al. | 606/232 |

FOREIGN PATENT DOCUMENTS

| | | | |
|---|---|---|---|
| 0 230 937 | 1/1987 | European Pat. Off. | A61B 17/08 |
| 0 611 567 | 8/1994 | European Pat. Off. | A61F 2/08 |
| 26 02 900 | 7/1977 | Germany | A61B 17/18 |
| 9201974 | 11/1992 | Netherlands | A61B 17/58 |
| WO 89/01767 | 3/1989 | WIPO | A61F 5/04 |
| WO 92/17122 | 10/1992 | WIPO | A61B 17/58 |
| WO 95/22930 | 8/1995 | WIPO | A61B 17/00 |

*Primary Examiner*—Michael Buiz
*Assistant Examiner*—Daphna Shai
*Attorney, Agent, or Firm*—Flehr Hohbach Test Albritton & Herbert LLP

[57] ABSTRACT

A fixation apparatus including a body portion and a plurality of leg portions extending from the body portion. The body portion is resiliently deformable between an initial orientation and an insertion orientation upon application of a force to the body portion. The leg portions are oriented at an angle relative to the opposite leg portion when the body portion is in the initial orientation and the leg portions are substantially parallel when the body portion is moved to the insertion orientation for insertion of the leg portions into tissue. The leg portions at least partially return to the initial orientation when the force applied to the body portion is released such that the leg portions anchor the fixation apparatus to the tissue.

14 Claims, 7 Drawing Sheets

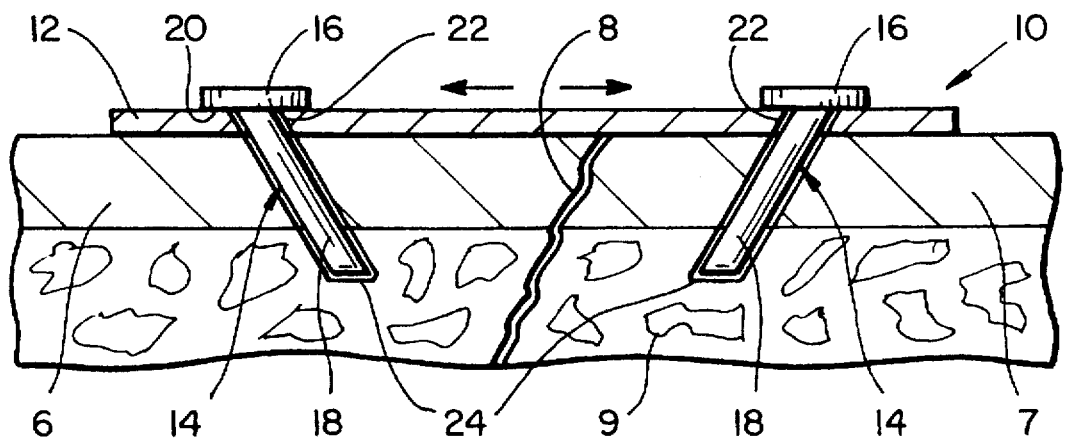
FIG_1
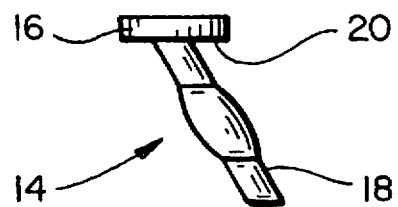
FIG_1A
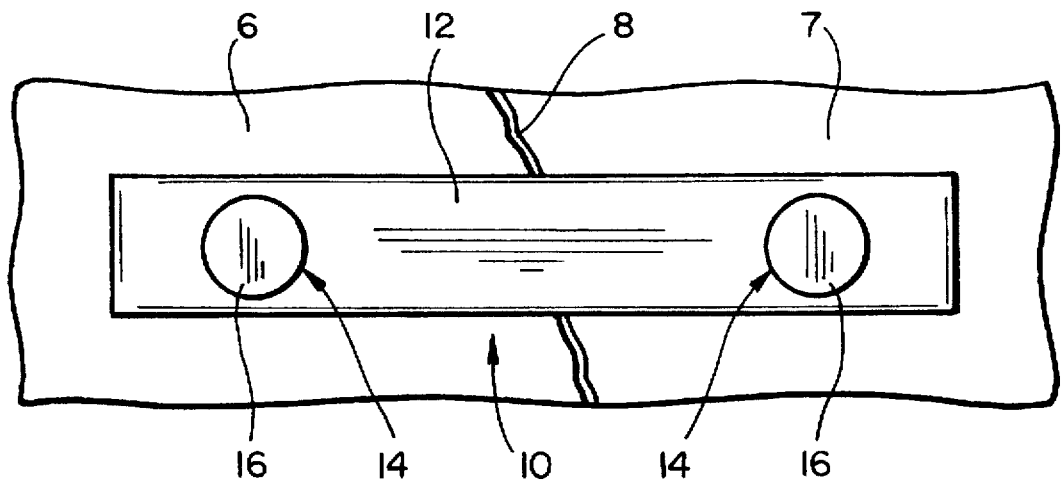
FIG_2

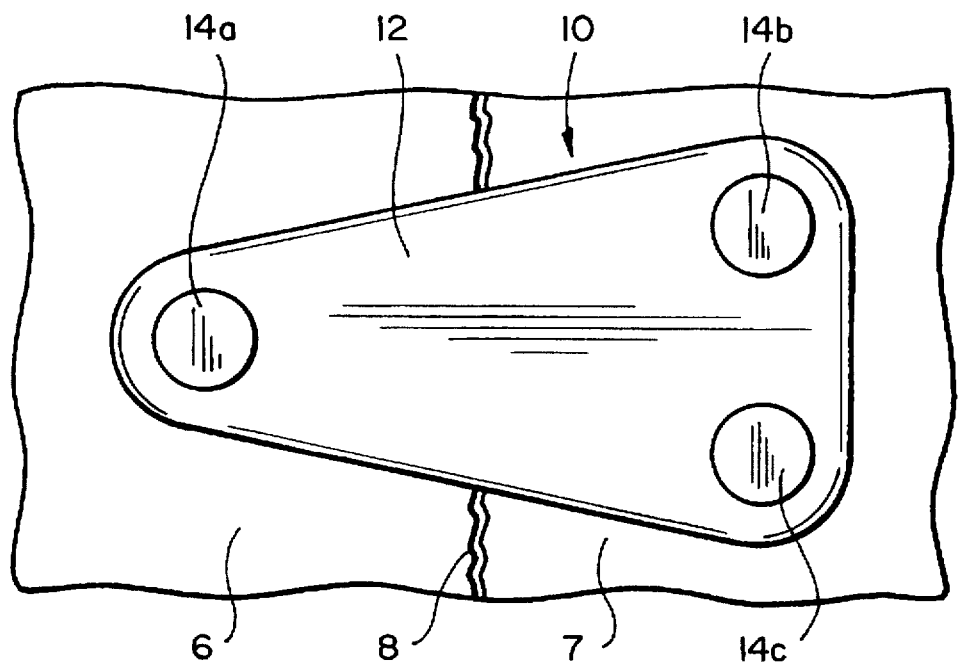
FIG_3
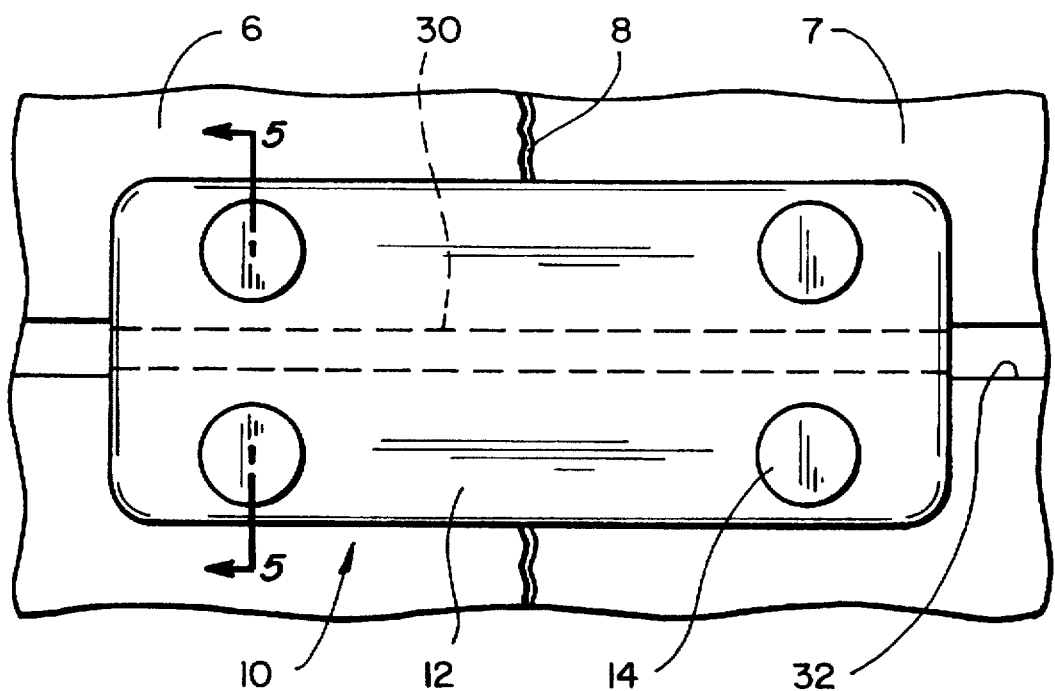
FIG_4

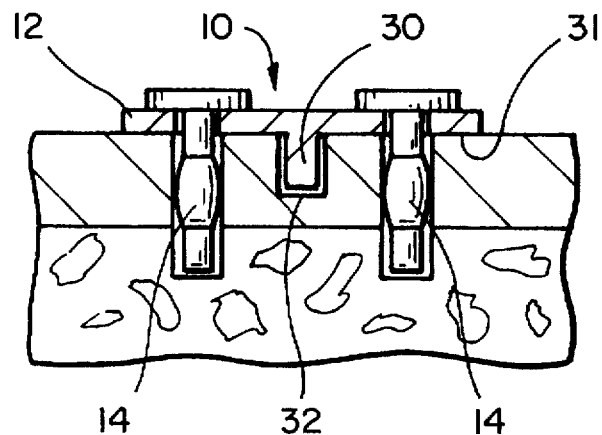
FIG_5
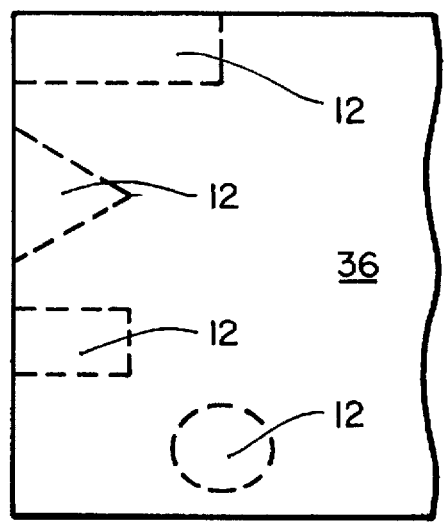
FIG_6
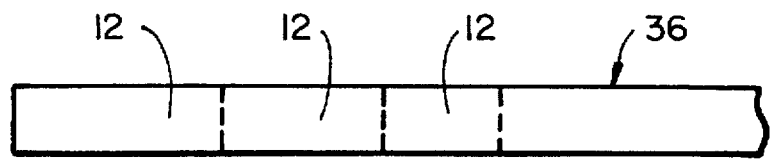
FIG_6A

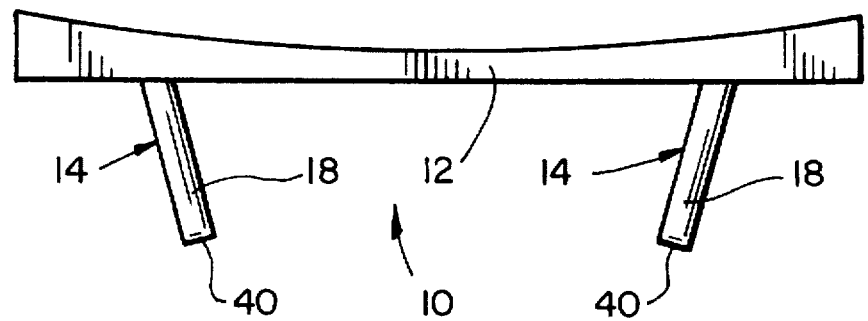
FIG_7
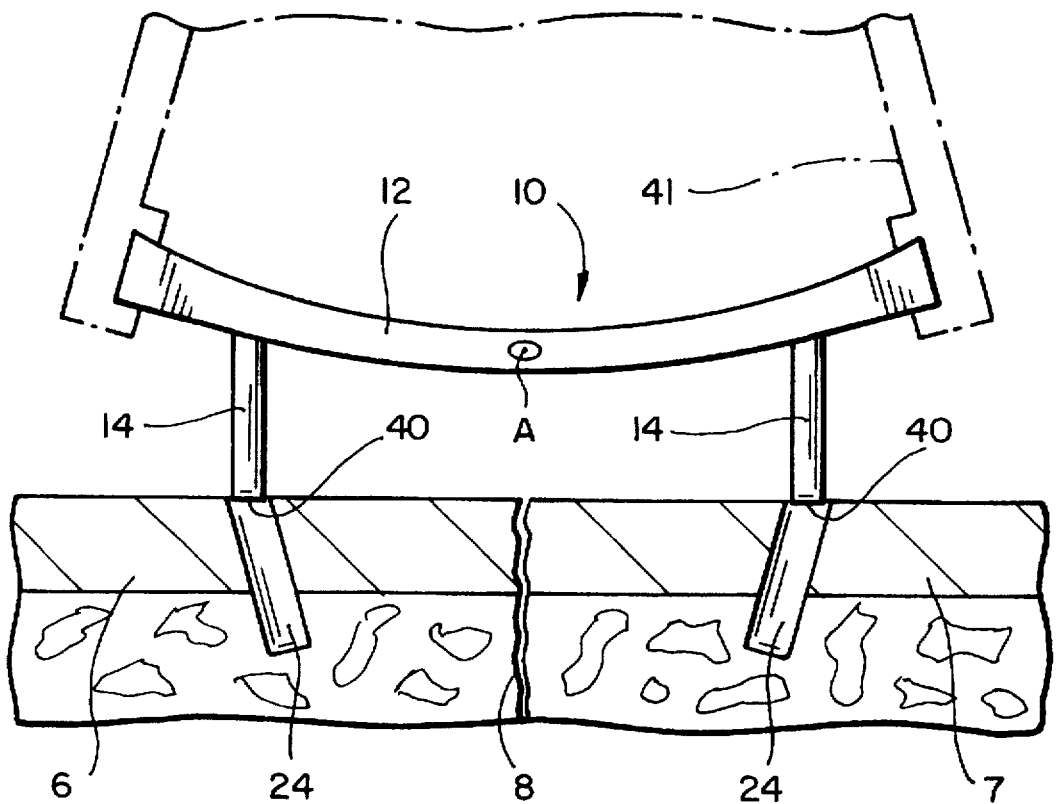
FIG_8

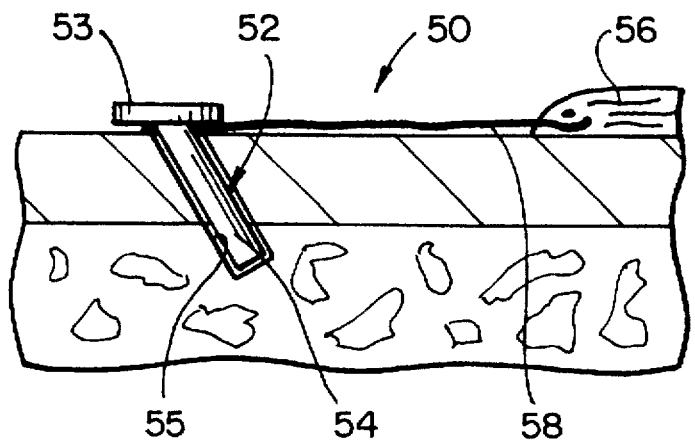
FIG_9
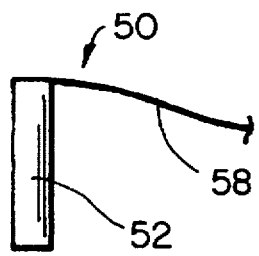
FIG_10
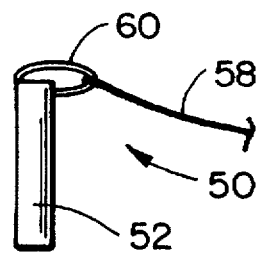
FIG_11
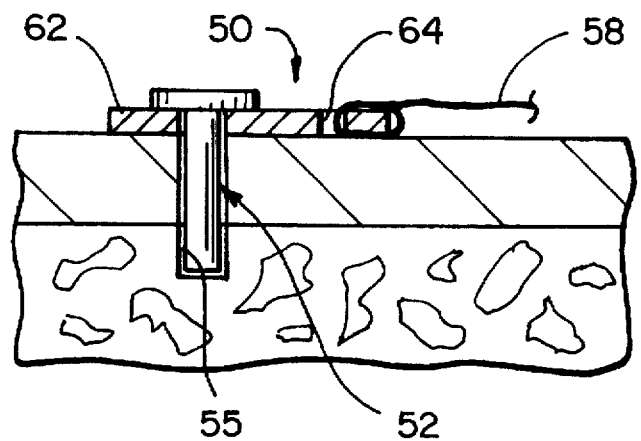
FIG_12

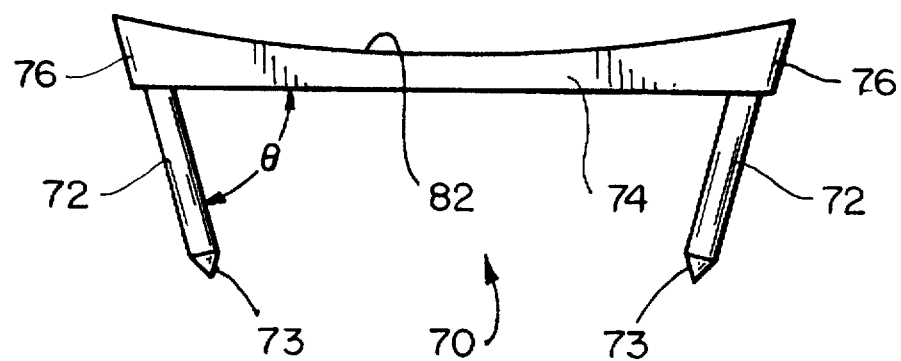
FIG_13
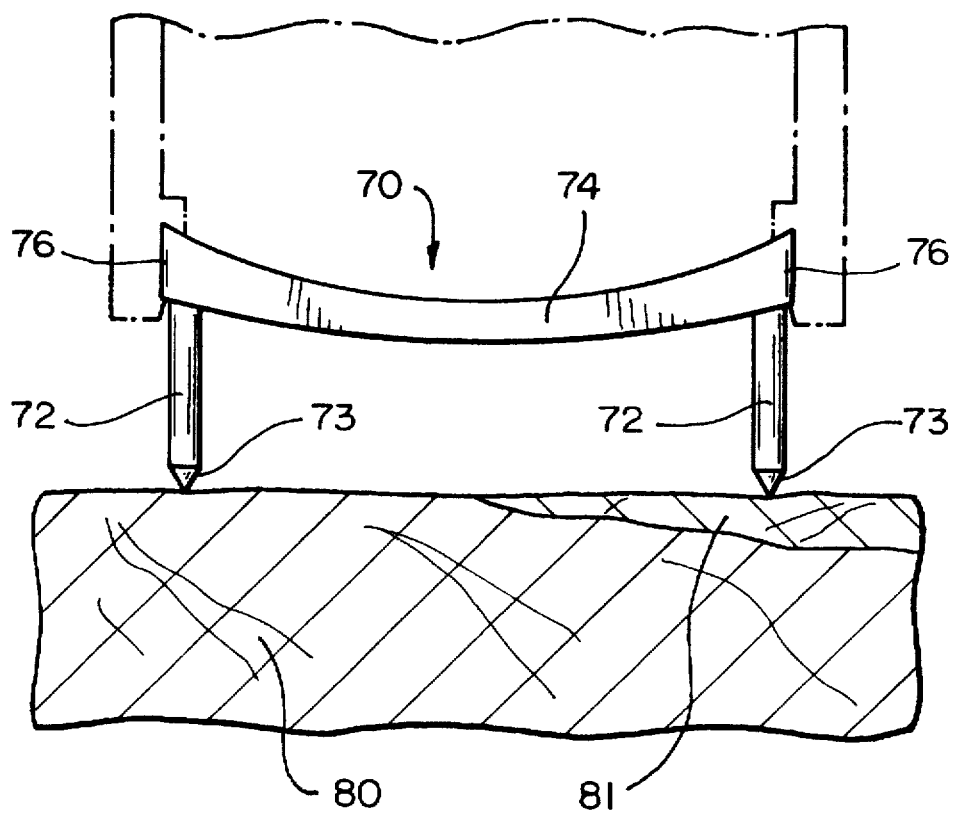
FIG_14

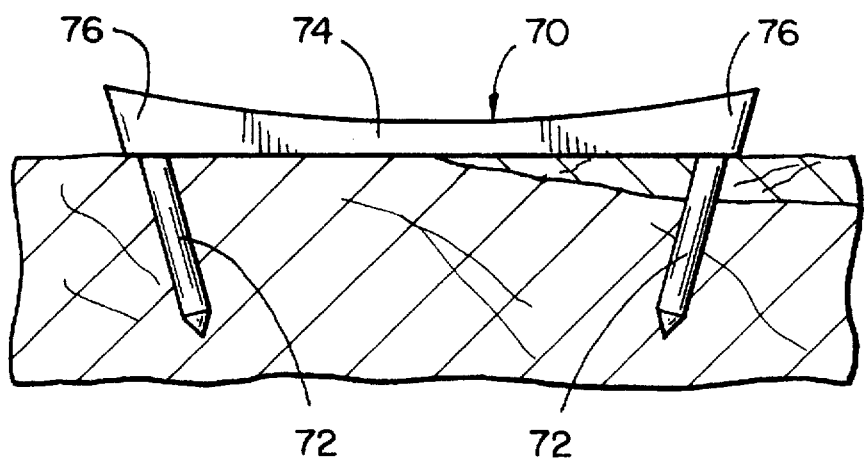
FIG_15
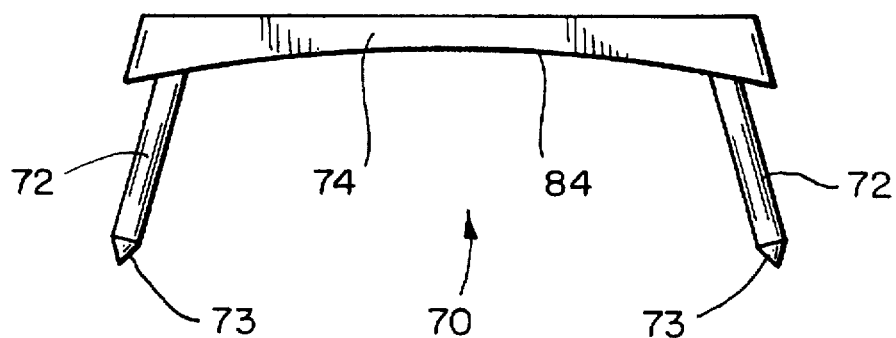
FIG_16
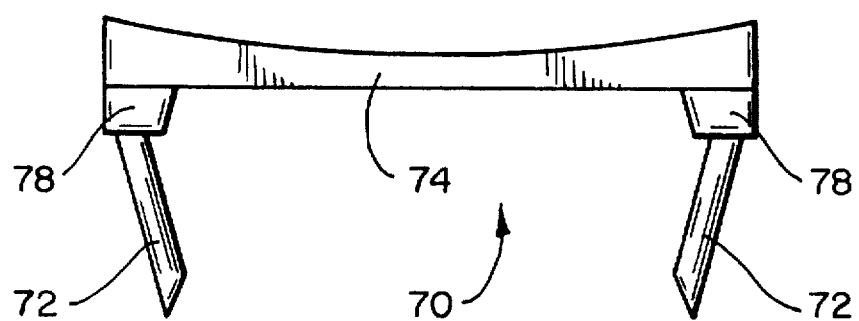
FIG_17

SURGICAL FIXATION APPARATUS

CROSS REFERENCE TO RELATED APPLICATION

This application is a continuation-in-part of U.S. Ser. No. 08/428,913 filed Apr. 25, 1995 now U.S. Pat. No. 5,634,926, the disclosure of which is incorporated herein by reference.

BRIEF DESCRIPTION OF THE INVENTION

This invention relates in general to a surgical fixation apparatus and, more particularly, to an apparatus for the fixation of bone, soft tissue to bone, and soft tissue to soft tissue.

BACKGROUND OF THE INVENTION

Various surgical plates have been employed in the treatment of traumas to facial or cranial bone structure, plastic surgery, reconstructive facial surgery, and the like to hold the bone sections or fragments in place during the healing process. The surgical plates are positioned against the surface of the bone sections which must be held together and fixed to the bone by mechanical fasteners such as bone screws, wire sutures or other fasteners which secure the plate to the bone surface. The fasteners are securely pressed or embedded in the bone to prevent the surgical plates from being pulled away from the surface of the bone sections. U.S. Pat. Nos. 4,966,599 and 5,290,281 disclose examples of bone stabilization plates which are secured to the bone structure, for example facial or cranial bones, by bone screws. U.S. Pat. No. 4,655,203 discloses a surgical device for immobilization of bone fracture which includes a stiff plate and stiff fixing elements which may be pressed into notches formed in the bone.

In such procedures as rotator cuff surgery and hand tendon surgery, tendons or other soft tissues are fixedly secured to bone. The tendons or other tissue are often secured to bone by feeding the soft tissue through holes formed in the bone and suturing the tissue in place. Another method of securing soft tissue to bone employs a fixation device which essentially tacks the tendon to bone. Unless the tendon or other soft tissue is completely immobilized, the fixation device must be securely embedded in the bone to hold the tendon stationary against the bone surface, resisting those forces tending to pull the tendon away from the bone surface, until the tendon has become attached to the bone. Another method of securing tendons and other soft tissue to bone uses a fixation device with an attached suture. Once again, the fixation device must be securely embedded in bone to resist forces tending to pull the tissue away from the bone surface. In various facial surgery procedures, soft tissue is surgically lifted or moved and then secured to bone by suturing and the like to hold the tissue in the desired position during the healing process. These tissues are generally subjected only to gravitational forces or other forces parallel to the surface of the bone, they are not exposed to forces tending to pull the tissue outwardly away from the bone.

Surgical plates must be securely affixed to bones which may be exposed to various tensile and bending forces during the healing process to prevent the plate from being pulled outwardly away from the bone. If the fasteners do not securely engage the bone, the applied stresses may have a tendency to pull the fasteners from the bone. Facial and cranial bone sections, on the other hand, are generally not exposed to such tensile and bending stresses. Instead, the bone sections are primarily subjected to forces tending to spread the bone sections apart or to cause lateral slippage of the bone sections along the fracture line. Since the applied forces are substantially parallel to the bone surface, the fasteners need only anchor the surgical plates to the facial or cranial bones to hold the bone sections in place. The additional security provided by securely embedding the fastener in bone and actually securing the plate to the bone surface is often not required with facial and cranial bones and of bones at other sites.

Securely embedding screws, nails and the like in bone is a time consuming and labor intensive process, considerably extending the time required to complete the operation. Even when the fasteners are initially inserted into pre-drilled holes, care must be taken to ensure that the desired orientation of the fasteners is maintained. Moreover, embedding the fasteners in bone may subject the relatively fragile facial bones to additional unnecessary stress. Surgical fasteners such as screws and the like require expensive manufacturing techniques because of the small size of the fastener. Minimizing the size of the plate and fastener would minimize the size of the surgical area and the amount of bone which must be exposed. However, the reduced size of the screws and other fasteners is limited because the fasteners have sufficient strength to engage bone and securely attach the plate to the bone. Using a fixation device which anchors the surgical plate to the bone, but does not securely affix the plate to the bone surface, would avoid the disadvantages associated with embedding the fastener in bone. Such a fixation device would also be particularly useful in other types of procedures where the fixation apparatus may be employed to affix soft tissue to bone.

The attachment of soft tissue to soft tissue is required to close an incision or cut, to hold skin grafts in position through attachment at the edges of the graft, to avoid shearing motion of the graft relative to the wound surface through attachment of the graft at random to the underlying wound surface, as well as in a variety of other medical treatments including the fixation of tendons, fascia, and the like in deeper environments. Tissue to tissue attachment is typically achieved using sutures or surgical staples. Surgical staples initially have a U-shaped configuration, and are employed by using a tool to insert the legs of the staples into the skin and cause the legs to bend inwardly to hold the staple in place. After a sufficient amount of healing has occurred, the staples are withdrawn using a removal tool which causes the legs to unbend sufficiently to withdraw the staple from the tissue. A fixation apparatus for quickly and easily attaching soft tissue to soft tissue is desirable.

The surgical plates and associated fasteners employed for bone fixation have been fabricated of materials such as titanium, stainless steel, vitalium, chrome cobalt, and suitable bio-compatible polymeric materials. Unless removed by surgery, the plates and fasteners formed of these materials permanently remain in the patient's body. The surgical plates and internal fastening members may cause various unpredictable problems if left intact as the bone dynamically reacts to the foreign bodies over time by molding to the shape of the foreign body, forming deposits on the foreign body, and responding to stress. The foreign bodies also provide potential cites for infection. Migration of the foreign body presents another problem if the surgical plate and/or fasteners are left in the patient's body. This problem is of particular concern when the patient is an infant or young child, where the considerable amount of skull growth has resulted in significant migration of foreign body to the extent where the plate has entered the brain.

Forming the plate and/or fasteners of a material which may be absorbed by the body over time would allow the foreign materials to be removed from the patient's body without requiring a second operation. U.S. Pat. Nos. 5,655,203, 4,905,680, 4,966,599, 5,275,601 and 5,290,281 describe forming the surgical plates and/or fasteners of absorbable materials. Fabricating a bone screw or other mechanical fastener out of absorbable polymers is often difficult because the absorbable fastener has a tendency to prematurely slip from the bone. Moreover, because of their reduced size, forming absorbable bone screws for the fixation of plates to facial and cranial bones is even more difficult. To achieve the desired strength, the absorbable screws must be larger in size than a comparable metal screw. A fixation device for the fixation of surgical plates to bone which may be easily manufactured of an absorbable material and reliably used is highly desirable.

OBJECTS AND SUMMARY OF THE INVENTION

It is a primary object of this invention to provide a fixation apparatus for the surgical fixation of bone or soft tissue to bone.

It is another object of this invention to provide a fixation apparatus for the attachment of soft tissue to soft tissue.

It is another object of this invention to provide a fixation apparatus for anchoring a surgical plate, suturing element or other surgical member to bone.

It is yet another object of this invention to provide a fixation apparatus which may be quickly and easily attached to bone and/or soft tissue by the surgeon without subjecting the bone or tissue to unnecessary stresses.

It is still another object of this invention to provide a fixation apparatus in which the size of the post may be minimized.

It is a further object of this invention to provide a fixation apparatus which may be fabricated of materials which are absorbed by the body over time.

A more general object of this invention is to provide a fixation apparatus which may be economically manufactured and which may be efficiently and reliably employed in the fixation of surgical plates, suturing elements and other surgical members to bone or the attachment of tissue to tissue.

In summary, this invention provides a fixation apparatus which is particularly suitable for use in the fixation of bone and/or soft tissue to bone. In one modification of the invention, the fixation apparatus is a bone fixation apparatus which generally includes at least one post device having a leg portion configured for releasable insertion into a hole formed in bone. The leg portion is of sufficient length relative to the interior diameter of the hole to resist removal of the leg portion from the hole in the bone when forces substantially parallel to the outer surface of the bone are applied to the post device. The post device anchors a surgical member, such as a surgical plate or suturing element, to bone. In another modification of the invention, the fixation device includes a continuous, elongated sheet of surgical plate material which is divisible into a plurality of plate members each having an arbitrary length. The plate members are mountable to the bone by fastening devices such as the post device.

This invention also provides a fixation apparatus which is particularly suitable for the attachment of tissue to tissue. The fixation apparatus generally includes a body portion which is resiliently deformable between an initial orientation and an insertion orientation for inserting the fixation apparatus into tissue upon application of a force to the body portion. A plurality of leg portions, for example two leg portions, extend from the body portion. The leg portions are oriented at an angle relative to the opposite leg portion when the body portion is in the initial orientation, and are substantially parallel when the body portion is moved to the insertion orientation for insertion of the leg portions into tissue. The leg portions at least partially return to the initial orientation when the force applied to the body portion is released, with the leg portions anchoring the fixation apparatus to the tissue.

Additional objects and features of the invention will be more readily apparent from the following detailed description and appended claims when taken in conjunction with the drawings.

BRIEF DESCRIPTION OF THE DRAWINGS

FIG. 1 is an enlarged, fragmentary, cross sectional view of a fixation apparatus in accordance with this invention, shown fixed to two bone sections.

FIG. 1A is an enlarged, fragmentary view of a modified post device.

FIG. 2 is an enlarged, fragmentary, top plan view of the fixation apparatus and bone sections of FIG. 1.

FIG. 3 is an enlarged, fragmentary, top plan view of a fixation apparatus in accordance with another embodiment of the invention.

FIG. 4 is an enlarged, fragmentary, top plan view of a fixation apparatus in accordance with yet another embodiment of the invention.

FIG. 5 is a fragmentary, cross sectional view taken along line 5—5 of FIG. 4.

FIGS. 6 and 6A are schematic, top plan views of a fixation apparatus in accordance with another embodiment of the invention.

FIG. 7 is an enlarged, side elevational view of a fixation apparatus in accordance with another embodiment of the invention.

FIG. 8 is an enlarged, side elevational view of the fixation apparatus of FIG. 7, shown during application of the apparatus to the bone sections.

FIGS. 9 is a schematic, fragmentary, side elevational view of a fixation apparatus in accordance with another embodiment of the invention, shown securing soft tissue to bone.

FIGS. 10–12 are fragmentary, side elevational views of other modifications of the fixation apparatus shown in FIG. 9.

FIG. 13 is an enlarged, side elevational view of a fixation apparatus in accordance with another embodiment of the invention.

FIG. 14 is an enlarged, side elevational view of the fixation apparatus of FIG. 13, shown prior to insertion of the apparatus into tissue.

FIG. 15 is an enlarged, side elevational view of the fixation apparatus of FIG. 13, shown inserted into tissue.

FIGS. 16 and 17 are enlarged, side elevational views of modifications of the fixation apparatus of FIG. 13.

DETAILED DESCRIPTION OF THE INVENTION

Reference will now be made in detail to the preferred embodiment of the invention, which is illustrated in the accompanying figures. Turning now to the drawings, wherein like components are designated by like reference numbers throughout the various figures, attention is directed to FIGS. 1 and 2.

A fixation apparatus 10 incorporating this invention may be used for the fixation of bone or soft tissue to bone. In the modification of FIGS. 1 and 2, the bone fixation apparatus 10 is shown holding two bone sections 6 and 7 in a desired position about a fracture line or incision, generally designated 8. Fixation apparatus 10 may be used with any type of bone structure as for example cancellous bones with marrow 9, bones without marrow such as the walls of the sinus, and the skull which includes an outer table, an inner table and marrow between the inner and outer tables. Preferably, the fixation apparatus 10 of the invention is used with bones which are subjected primarily to forces parallel to the bone surface, such as those which tend to separate the bone sections or cause relative lateral movement of the bone sections. The bones are generally isolated from forces transverse to the bone surface and are not required to carry a significant load. Examples of such bones include the facial and cranial bones, although it will be understood that use of the bone fixation apparatus may also be used with other suitable bones.

In the embodiment shown in FIG. 1, fixation apparatus 10 includes a surgical plate member 12 extending across the surface of the bone and post devices 14 retaining plate member 12 in place. The shape, size and thickness of plate member 12 is subject to considerable modification depending upon the location of bone sections 6 and 7, the size of fracture line 8, the characteristics of the material of plate member 12, the characteristics and desired result of the surgical procedure employing the apparatus and the like. Surgical plate member 12 is anchored to each bone section by at least one post device 14. In many applications, using one post device 14 per bone section as shown in FIGS. 1 and 2 will sufficiently retain the bone sections in the desired position. However, using more than one post device for at least one of the bone sections offers the advantage of increased stability and augmented parallelographic force. For example, FIG. 3 shows a modification of the invention where one post device 14a anchors plate member 12 to bone section 6 and two post devices 14b and 14c anchor the plate to bone section 7. The positioning of post devices 14a, 14b and 14c creates a triangulation effect which substantially resists relative lateral movement of the bone sections along the fracture line. Instead of using three post devices 14 for enhanced stability as shown in FIG. 3, a greater number of post devices 14 may be employed if desired.

If additional security is desired, plate member 12 may be secured to bone by replacing one of the post devices 14, for example post device 14a shown in FIG. 3, with a screw or other suitable fastener which securely engages the walls of hole 24 to attach the plate member to the surface of the bone section. The remaining post devices, such as post devices 14b and 14c, anchor the plate member 12 to the other bone section to retain the bone sections in the desired position.

As shown in FIG. 1, post device 14 includes an enlarged cap or end portion 16 and a leg portion 18 depending from the underside 20 of end portion 16. The leg portion 18 extends through an aperture 22 formed in plate member 12 and is positioned in a hole 24 formed in bone sections 6 and 7 to anchor surgical plate 12 to the bone sections. Unlike the fixation devices of the prior art, post device 14 is not intended to prevent the surgical plate 12 from being pulled away from the surface of the bone sections. Instead, post device 14 substantially resists forces parallel to the surface of the bone, such as those tending to separate the bone sections or cause lateral slippage along the fracture line, to hold surgical plate 12 in place. Leg portion 18 is formed of sufficient length relative to the interior diameter of the hole 24 to resist those forces parallel to the bone surface. The optimum length for leg portion 18 depends in part on such factors as the stiffness of the material used in the fabrication of post device 14 and the magnitude of the forces applied to the post device. For many applications, a length of at least about two times the interior diameter of the hole 24 will be sufficient to prevent forces parallel to the bone surface from deforming the leg portion and pulling the leg portion 18 from the bone. However, it will be understood that in some applications of the invention it may be desirable to provide leg portion 18 with a lesser or greater length or angle.

Since it is the length of the leg portion 18 which holds the post device 14 in the hole and anchors the plate member 12 to the bone sections, leg portion 18 may be shaped so that only a minimum amount of pressure is required to slip the leg portion into the hole 24. The leg portion 18 is not securely embedded in place, but is instead movable in a direction parallel to the axis of the hole. The exterior of leg portion 18 may be substantially cylindrical as shown in FIG. 1, or, if desired, leg portion 18 may be configured to provide a limited area of engagement between the exterior of the leg portion and the walls of hole 24. For example, FIG. 1A shows a modification of post device 14 having a slightly bowed or spindle-shaped cross section, although it is to be understood that leg portion 18 may have other cross sectional shapes if desired. Moreover, the area of limited engagement need not extend around the entire circumference of the leg portion 18. Instead, leg portion 18 may be formed with one or more projections which are configured to slightly engage the interior wall of hole 24.

The maximum diameter of the spindle-shaped leg portion shown in FIG. 1A is preferably equal to or slightly greater than the interior diameter of the hole 24 so that when the post device 14 is initially inserted in the hole, the leg portion will partially engage the wall of the hole. Although the limited engagement between the leg portion and wall of the bone is generally insufficient to securely retain the post in the hole 24, the spindle shape of leg portion 18 allows the surgeon to conveniently manipulate the surgical plate relative to the bone sections during the surgical procedure without pulling the post device from the hole 24. Since only a limited area of leg portion 18 engages the walls of the bone, the pressure required to insert the post device 14 into hole 24 is not significantly increased.

As is shown particularly in FIG. 1, leg portion 18 is preferably oriented at an angle of about 15 to 55 degrees relative to the underside 20 of the end portion 16. For optimum effectiveness, the angled leg portion 18 is inserted into a hole 24 extending into the bone at approximately the same angle as the inclination of leg portion 18 so that the underside 20 of the end portion engages the upper surface of the plate member 12. Aperture 22 may also extend through plate member 12 at an angle. When post device 14 is inserted in the bone, the angled leg portion 18 is preferably oriented so that the tip of the leg portion points in a direction opposite the forces applied to the bone section. For example, in FIG. 1 the angled leg portion 18 is oriented inwardly toward the fracture line, extending in a direction opposite those forces tending to pull the bone sections 6 and 7 apart.

Providing post device 14 with a slanted leg portion increases the stability of bone fixation apparatus 10 in resisting forces parallel to the bone sections 6 and 7. When positioned as shown in FIG. 1, the slanted leg portions of the post devices 14 on opposite sides of the fracture line may also be used to urge the bone sections 6 and 7 together. Urging the bone sections together with post devices 14 ensures the bone sections are held together, facilitating the healing process. Although angled leg portions 18 increase the ability of post device 14 to resist forces substantially parallel to the bone sections, it will be understood that the leg portions 18 may also be perpendicular to the underside of end portion 16 if desired.

The bone fixation apparatus 10 may be applied to the selected bone sections using a suitable surgical technique. Apertures 22 may be formed in plate member 12 at predetermined locations or, if desired, the surgeon may select the site of the apertures. If desired, the apertures 22 and holes 24 may be formed simultaneously by locating the plate member 12 on the bone sections 6 and 7 and drilling through the plate and bone. However, forming the apertures 22 separately from the holes 24 isolates the wound or surgical site from unwanted surgical plate fragments. The locations of holes 24 may be selected using a template if desired. Preferably, holes 24 are formed using a drill or other appropriate instrument having a stop or collar limiting the hole depth to avoid excess penetration particularly in the skull. When post devices 14 having angled leg portions 18 are employed, the stop is preferably oriented at an angle relative to the drill bit similar to the angle between the end portion 16 and leg portion 18. Alternatively, the stop may be curved for usage with post device angled or perpendicular to the end portion 16.

The configuration of surgical plate member 12 is subject to considerable variation depending upon the constraints of a particular application. FIG. 2 shows a plate member 12 having a substantially rectangular shape. The plate member may also have other shapes such as the triangular shape shown in FIG. 3. FIGS. 4 and 5 show another embodiment of the invention in which plate member 12 includes a flange or rib 30 depending from the underside 31 of the plate member 12. In the embodiment shown in FIGS. 4 and 5, the flange 30 extends continuously along the entire length of the plate member. However, flange member 30 may have other configurations if desired. Flange 30 is positioned in a thin groove or cut 32 formed in the bone to assist in obtaining the desired positioning of fixation apparatus 10 and bone sections 6 and 7 when the apparatus 10 is initially anchored to the bone. The interengagement of flange 30 and groove 32 also provides additional resistance against relative lateral slippage between the bone sections 6 and 7. In the modification shown in FIGS. 4 and 5, four post devices 14 having a spindle-shaped cross section are employed to anchor plate member 12 to bone. The post devices 14 may have slanted leg portions or leg portions substantially perpendicular to the plate member 12.

Although not shown, the plate member may also be formed with a curved or stepped cross-section. The curved or stepped configuration may be prefabricated or the plate member may be formed of a suitable material and manipulated into the desired shape by the surgeon or surgical assistant. The prefabricated plate member may also be formed of a material which allows the shape of the plate member to be adjusted during the operation.

FIG. 6 illustrates a modification of the invention in which plate member 12 comprises a section of an elongated sheet 36 of surgical plate material. The sheet 36 shown in FIG. 6 is of sufficient width to allow the surgeon to select any shape desired for the surgical plate. Alternatively, as is shown in FIG. 6A the sheet 36 may be formed as a narrow strip of material which may be separated into plate sections of arbitrary lengths. The ability to divide the sheet 36 of plate material into plate sections each having an arbitrary shape provides the surgeon with immediate access to a plate member 12 of appropriate size. The sheet 36 of surgical plate material may be divided into separate plate sections using the appropriate clipping tools for the particular material of sheet 36. Depending upon the material employed for surgical sheet 36, the sheet 36 may be retained in a roll or provided as a planar sheet of material. As with the previously described embodiments, apertures may be pre-formed in sheet 36 or the apertures may be formed by the surgeon at the desired locations. Alternatively, as will be described in greater detail in relation to FIGS. 7 and 8, sheet 36 may be integrally formed with a plurality of spaced post devices 14.

Turning to FIGS. 7 and 8, fixation device 10 is a monolithic structure in which post devices 14 are integrally formed with plate member 12. In the modification shown in FIGS. 7 and 8, the leg portions 18 of the post devices 14 are oriented at an angle relative to the underside of plate member 12. The fixation apparatus is applied to bone by deforming the edges of plate member 12 upwardly about an axis A extending through the body portion between the legs as shown in FIG. 8 to position the tips 40 of the post device above the open ends of the holes 24. Preferably, the upper surface of the plate 12 is concave to facilitate deformation of the plate to bring the post devices 14 into a substantially parallel orientation. The post devices 14 are then slipped into the holes and the plate member 12 is moved toward the bone surface. The plate member 12 returns to its original shape shown in FIG. 7, with the angled post devices 14 providing addition resistance against separation, when the outer edges of the plate member are released and the plate member is positioned against the bone surface. Preferably, a surgical instrument 41 is used to bend the plate 14 and hold the plate as shown in FIG. 8, allowing a nurse or surgical technician to prepare the plate for insertion and allowing the surgeon to manipulate the plate to the desired position. The surgical instrument may also be used to adjust the position of the fixation apparatus or to remove the fixation apparatus from the bone.

The post devices 14 anchor the fixation apparatus to bone to retain the bone sections in the desired position during healing. As previously described, the angled leg portions 18 provide increased resistance to oppose forces substantially parallel to the bone surface and retain the bone sections in place. In the present embodiment, the post devices are preferably oriented at an angle of approximately 10–20 degrees to minimize the amount of deformation of plate 12 which is required to insert the post devices 14 into holes 40.

Although slanted leg portions 18 are preferred for increased stability, post devices 14 may also extend in a direction substantially perpendicular to the underside of the plate member 12. With the perpendicular post devices 14, upward deformation may not be required to align the tips 40 of the post devices with the holes 24 formed in the bone sections.

In the previously described embodiments of the invention, fixation apparatus 10 was particularly suitable for the fixation of bone to bone. FIGS. 9–11 show alternative embodiments of the invention where fixation apparatus 10 is employed to affix or anchor soft tissue to bone. Turning to FIG. 9, fixation device 50 includes a post device 52 having an enlarged end portion 53 and a leg portion 54 which may be slipped into a hole 55 formed in bone. The leg portion 54 of the post device 52 is of sufficient length to substantially resist forces substantially parallel to the surface of the bone, providing an anchor for securing soft tissue to bone. As with the embodiments of FIGS. 1–8, leg portion 54 is preferably formed so that it slips into hole 55 with minimal force. If desired, the leg portion 54 may be shaped to provide a limited area of engagement with the walls of the hole 55 to allow the surgeon to conveniently manipulate the fixation apparatus 50 without pulling leg portion 54 from hole 55.

A suturing element 58 having one end coupled to the post device 52 is used to attach the soft tissue, generally designated 56, to the post device 52. The suturing element 58 may be coupled to the post device 52 by tying or wrapping the suturing element around the leg portion below the enlarged end 53. Alternatively, post device 52 may be integrally or monolithically formed with the suturing element 58 as shown in FIG. 10 or the post 52 may be formed with ring 60 to which suturing element 58 may be attached as is shown in FIG. 11. In the modification shown in FIG. 12, post device 52 anchors a surgical plate 62 to the bone and the suturing element 58 is secured to the surgical plate 62. In the modification shown in FIG. 11, the suturing element is passed through aperture 64 and tied to the plate 62. It will be understood that other means in accordance with the invention may also be employed to affix the suturing element to the surgical plate or the post. Although not shown, the post device may be inserted through an aperture formed in the suturing plate or other similar surgical member as a tack. The opposite end of the suturing element may be attached to the soft tissue 56, as shown in FIG. 9. Alternatively, the opposite end of the suturing element may be secured to a second fastening element, with the soft tissue being supported by the loop of the suturing element between the secured ends. The post device and suturing element of the present invention secure the soft tissue to the post device and hold the tissue in the desired position by essentially suspending the tissue from the anchored post device. By adjusting the length of the suturing element and the position of the post device, fixation apparatus 50 may be conveniently employed to hold the soft tissue in the desired position during the healing process.

With this invention, the post devices anchor the surgical member, such as the surgical plate or suturing element, to bone without securely engaging the bone and attaching the surgical member to the bone surface. The size of the post device may be minimized. For example, the post device may have a leg diameter on the order of about 1 mm.

FIGS. 13-15 show another embodiment of a fixation apparatus in accordance with this invention. Fixation apparatus 70 is particularly suitable for the attachment of tissue to tissue, including surface applications where fixation apparatus 70 is used for example to close an incision or to attach or stabilize a skin graft, as well as deeper applications where the fixation apparatus 70 is used for example in the fixation of tendons, fascia, fibrous structures or implantable devices. The fixation apparatus 70 is preferably formed of a suitable bio-compatible or material which is absorbed by the body over time, or a yet unknown material in the rapidly developing science of bio-compatible materials. The specific type of absorbable material employed will depend upon a variety of factors including the length of time during which the fixation apparatus 70 must securely retain the tissue in place for proper healing to occur.

As is shown particularly in FIG. 13, in this embodiment of the invention the fixation device 70 generally includes a plurality of leg portions 72 depending from a connecting body portion 74. Although shown two in number, it is to be understood that the fixation device 70 may include a greater number of leg portions if desired, with the body portion 74 in these other modifications being shaped to join the leg portions. Leg portions 72 are preferably oriented at an angle θ relative to the body portion 74, for example an angle of about 5° to 40° although it is to be understood that the angle of leg portion 74 may be greater than 40° if desired. The leg portions 72 may be directed inwardly toward the opposite leg portion as shown in FIG. 13. Alternatively, the leg portions 72 may be directed outwardly as is shown in FIG. 16 to encourage distraction. In these embodiment, the leg portions 72 have pointed tips 73 shaped to pierce the skin and/or other tissue and facilitate insertion of the leg portions 72 into the tissue. However, it is to be understood that the ends of the leg portions 72 may also be blunt, tapered or have other shapes if desired.

As discussed above in relation to the embodiment of FIGS. 7 and 8, the fixation apparatus 70 is implanted by engaging the opposed ends 76 with the arms 77 of an instrument and applying a compressive force to the body portion 74 to manipulate the leg portions 72 from the initial orientation shown in FIG. 13 to parallel orientation as shown in FIG. 14. Although leg portion 72 are preferably substantially parallel for installation to optimize the ease with which the leg portions may be inserted into the tissue, it is to be understood that positioning the leg portions at an angle of about 0° to 5° relative to the parallel planes may be sufficient to insert leg portions 72 into tissue.

After the leg portions 72 have been inserted into the tissue, the body portion 74 is released and allowed to relax, causing the leg portions to return at least partially to the initial position as is shown for example in FIG. 15. In FIG. 15, the fixation apparatus is used to hold tissue sections 80 and 81 together, although it is to be understood that the use of the fixation apparatus is not to be limited to the application shown in FIG. 15. In the relaxed position, the leg portion 72 anchor the fixation apparatus 70 in the tissue, substantially resisting outward migration of the leg portions 72 from the tissue. The fixation apparatus 70 holds the tissue in place during the healing process. With the inward directed configuration of FIGS. 13-15, the relaxed leg portions also urge the sections of tissue together. In addition to anchoring the fixation device 70 in place, the angled orientation of the leg portions 72 also facilitates the healing process.

The fixation apparatus 70 may be removed by applying a compressive force to the opposed ends 76 of the body portion to return the leg portions to the generally parallel orientation of the installation configuration shown in FIG. 14 and pulling the leg portions 72 from the tissue. Alternatively, the fixation apparatus 70 may be removed by inserting a flat tool beneath the body portion 74 and lifting the fixation apparatus from the tissue. FIG. 17 shows a modification of the invention which is particularly suitable for this removal technique. The leg portions include an enlarged collar 78 positioned proximate the body portion. The collar 78 engages the tissue surface to prevent further insertion of the leg portions 72 into the tissue. The height of the collar 78 is selected so that when the legs 72 are inserted into tissue, the underside or lower surface of the body portion 74 is spaced from the tissue surface. A suitable tool may be inserted into the gap between the tissue surface and the body portion and used to pry the fixation apparatus 70 from the tissue. Another advantage of the collars 78 is that separating the body portion 74 from the tissue surface minimizes or eliminates any imprint left in the skin by the fixation apparatus 70.

The shape of body portion 74 is subject to considerable variation. In the embodiment shown in FIGS. 13-15, the body portion 74 includes a concave upper surface 82, providing the body portion 74 with enlarged ends 76 and a thinner middle section. This configuration facilitates the bending of the fixation apparatus and the insertion of the fixation apparatus into tissue and/or bone. For the fixation apparatus shown in FIG. 16, where the legs are initially directed outwardly, the lower surface 84 is preferably concave. However, it is to be understood that in other embodiments of the invention neither surface may be concave.

As is apparent from the foregoing description, the fixation apparatus of the present invention is particularly suitable for holding bone sections or soft tissue in the desired position. The fixation apparatus of the present invention may be formed of any suitable bio-compatible or absorbable materials. Examples of suitable materials include, but are not limited to, bio-compatible metals, bio-compatible elastomers exhibiting sufficient stiffness properties and other bio-compatible polymers, and bio-absorbable polymers which are partially or completely absorbed by the body after time may also be used.

What is claimed is :

1. A fixation apparatus comprising:

a body portion, a plurality of leg portions unitary with said body portion, and extending from said body portion at an angle relative to the opposite leg portion in an initial orientation;

said body portion being deformable about a middle portion between said leg portions to move said leg portions from the initial orientation to an insertion orientation in which said leg portions are substantially parallel for insertion of said leg portions into tissue or bone, said leg portions at least partially returning to the initial orientation when the force applied to said body portion is released such that said leg portions anchor said fixation apparatus to the tissue or bone.

2. The fixation apparatus of claim 1 in which said body portion has first and second opposed ends, said body portion being resiliently deformable for movement of said leg portions between the initial orientation and the insertion orientation upon application of a force to said opposed ends of said body portion.

3. The fixation apparatus of claim 1 in which said body portion has an upper surface and a lower surface from which said leg portions extend, one of said upper surface and said lower surface being concave to facilitate the resilient deformation of said body portion.

4. The fixation apparatus of claim 1 in which said leg portions are directed inwardly toward the opposite leg portion when said body portion is in the initial orientation.

5. The fixation apparatus of claim 1 in which said leg portions are directed outwardly away from the opposite leg portion when said body portion is in the initial orientation.

6. The fixation apparatus of claim 1 in which said body portion has an underside and said leg portions are orientated at an angle in the range of 5° to 40° relative to the underside of the body portion.

7. The fixation apparatus of claim 1 in which said leg portions have pointed tips configured to pierce tissue.

8. The fixation apparatus of claim 1 in which said body portion has an underside and said leg portions include an enlarged collar proximate said body portion, said collar including a lower surface spaced from the underside of said body portion and configured to engage the surface of the tissue and prevent further insertion of said leg portions into the tissue such that the underside of said body portion is spaced from the tissue when said leg portions are inserted therein.

9. The fixation apparatus of claim 1 in which said fixation apparatus includes two leg portions.

10. The fixation apparatus of claim 1 in which said body portion and leg portions are formed of an absorbable material.

11. The fixation apparatus of claim 1 in which said leg portions are monolithically formed with said body portion.

12. In combination, the fixation apparatus of claim 1 and an instrument engaging said plate member and retaining said plate member in said insertion orientation.

13. A method of attaching tissue to tissue comprising the steps of:

providing a fixation apparatus having an body portion and leg portions unitary with said body portion, and extending from said body portion in an initial orientation with said leg portions oriented at an angle relative to the opposite leg portion;

applying a force to said body portion to resiliently deform said body portion to move said leg portions from the initial orientation to an insertion orientation with said leg portions being substantially parallel;

after said body portion has been resiliently deformed to the insertion orientation, inserting said leg portions into the tissue;

after insertion of said leg portions into the tissue, releasing said body portion so that said leg portions at least partially return to the initial orientation to anchor said fixation apparatus to the tissue.

14. The fixation apparatus of claim 13 in which said step of applying a force to said body portion includes engaging opposite ends of said body portion with an instrument and actuating said instrument to apply a compressive force to said opposite ends of said body portion.

* * * * *